United States Patent
Tanimoto

(10) Patent No.: US 9,222,066 B2
(45) Date of Patent: Dec. 29, 2015

(54) INCUBATOR AND METHOD FOR DECONTAMINATING INCUBATOR

(71) Applicant: Shibuya Kogyo Co., Ltd., Ishikawa (JP)

(72) Inventor: Kazuhito Tanimoto, Ishikawa (JP)

(73) Assignee: SHIBUYA KOGYO CO., LTD., Ishikawa (JP)

(*) Notice: Subject to any disclaimer, the term of this patent is extended or adjusted under 35 U.S.C. 154(b) by 0 days.

(21) Appl. No.: 14/539,135

(22) Filed: Nov. 12, 2014

(65) Prior Publication Data

US 2015/0139855 A1    May 21, 2015

(30) Foreign Application Priority Data

Nov. 18, 2013    (JP) ................. 2013-237995

(51) Int. Cl.
    *C12M 1/12*     (2006.01)
    *C12M 1/00*     (2006.01)
    *A61L 2/20*     (2006.01)

(52) U.S. Cl.
    CPC ............. *C12M 37/02* (2013.01); *A61L 2/208* (2013.01); *C12M 29/04* (2013.01); *C12M 29/20* (2013.01); *C12M 37/00* (2013.01); *C12M 39/00* (2013.01); *C12M 41/14* (2013.01)

(58) Field of Classification Search
    CPC .......... A61L 2/20; A61L 2/208; C12M 41/14; C12M 1/12
    See application file for complete search history.

(56) References Cited

U.S. PATENT DOCUMENTS

| 2009/0221064 A1 | 9/2009 | Osawa et al. |
| 2011/0189765 A1 | 8/2011 | Fukui et al. |
| 2012/0275967 A1 | 11/2012 | Yokoi et al. |
| 2013/0336844 A1 | 12/2013 | Yokoi et al. |

FOREIGN PATENT DOCUMENTS

| EP | 2210618 | 7/2010 |
| EP | 2354216 | 8/2011 |
| EP | 2517735 | 10/2012 |
| JP | 2011-50289 | 3/2011 |
| JP | 2011-160672 | 8/2011 |
| JP | 4799221 | 10/2011 |

OTHER PUBLICATIONS

Search report from E.P.O., mail date is Mar. 30, 2015.

*Primary Examiner* — Sean E Conley
(74) *Attorney, Agent, or Firm* — Greenblum & Bernstein, P.L.C.

(57) ABSTRACT

An incubator includes filters in supply passages for supplying an environment-adjusting-medium. Divergent passages are connected to portions of the supply passages upstream from the filters. The divergent passages converge to a single supply/exhaust passage, which is provided with a pump. By driving the pump in a forward or reverse direction, decontamination gas is pumped from a culture space and discharged outside, and open air is introduced into the culture space. After sucking the contamination gas to adsorb it on the filter, open air is introduced so that the contamination gas is discharged into the culture space 6.

3 Claims, 4 Drawing Sheets

INCUBATOR AND METHOD FOR DECONTAMINATING INCUBATOR

BACKGROUND OF THE INVENTION

1. Field of the Invention

The present invention relates to an incubator having a culture space for accommodating a cultured object such as a cell being cultivated, it particularly relates to an incubator supplying $CO_2$ gas, $N_2$ gas, water for humidification and so on through a filter, and it relates to a method for decontaminating the incubator.

2. Description of the Related Art

In an incubator, in which cultivation is carried out with accommodating cells, microbes, and so on in a culture space, it is necessary to decontaminate the inside of the incubator and create an aseptic condition before accommodating the cells and so on in the culture space. Thus, decontamination gas such as hydrogen peroxide gas ($H_2O_2$ gas) is introduced from a decontamination gas supply device into the culture space to decontaminate and maintain an aseptic environment inside of the culture space.

In an incubator used for cultivating cells and so on, carbon dioxide gas ($CO_2$ gas) or nitrogen gas ($N_2$ gas) having a predetermined concentration is supplied into the culture space provided in the incubator in order to create a suitable environment in the culture space for cell cultivation (see Japanese Patent No. 4799221), and water for humidification is supplied into the culture space in order to maintain the inside of the culture space at a constant humidity (see Japanese Unexamined Patent Publication No. 2011-160672).

A sterilization filter is provided in supply passages, through which $CO_2$ gas, $N_2$ gas, and water for humidification or the like (hereinafter, these are referred to as the environment-adjusting-media) are supplied to the culture space, so that the environment-adjusting-media are supplied through the filters. Further, for maintaining the sterilization of the culture space, these filters should be sterilized.

In a device disclosed in Japanese Patent No. 4799221, the sterilization of the inside of the cultivation space of the incubator is carried out at the same time when the inside of a chamber of the isolator is sterilized. Namely, the decontamination gas is introduced from the isolator into the incubator by opening the door between the isolator and the incubator. At this time, the decontamination gas in the culture space is sucked from a sampling pipe, and introduced to pipes for supplying $CO_2$ gas and $N_2$ gas through branching pipes, to sterilize filters provided in the supply pipes.

In a device disclosed in Japanese Unexamined Patent Publication No. 2011-160672, the decontamination gas is sucked from the culture space to a water supply passage to decontaminate the filters. Therefore, it is not necessary to provide a pipe such as a sampling pipe. However, in such a construction, a filter sterilized by the decontamination gas can only be irradiated by ultraviolet rays using an ultraviolet lamp, so that the decontamination gas is sterilized.

In a device disclosed in Japanese Patent No. 4799221, a sampling circuit is utilized for decontamination of filters provided in supply pipes for $CO_2$ gas and $N_2$ gas. In the case of an incubator, which does not need to be provided with such a sampling circuit, pipes corresponding to the sampling circuit should be separately provided for sterilization, which increases the cost. Further, in a device disclosed in Japanese Unexamined Patent Publication No. 2011-160672, since the decontamination gas on the sterilized filters is only sterilized by using an ultraviolet lamp, $H_2O_2$ gas remains on the sterilized filters. If water for humidification is supplied to the filters, $H_2O_2$ gas is mixed with the water for humidification, and $H_2O_2$ gas can get mixed in with the moisture supplied into the culture space, which can destroy the culture environment.

SUMMARY OF THE INVENTION

An object of the present invention is to provide an incubator and a method for decontaminating the incubator, by which an optimum sterilized environment is formed while the decontamination gas, which has sterilized filters, does not remain on the filters.

According to the present invention, an incubator comprises an environment-adjusting-medium supply unit, a decontamination gas supply unit, a decontamination gas suction unit, and an open air introduction unit. The environment-adjusting-medium supply unit has a supply passage, through which the environment-adjusting-medium stored in a reservoir is supplied to a culture space accommodating a cultured object. The environment-adjusting-medium supply unit supplies the environment-adjusting-medium from the reservoir to the culture space through a filter arranged in the supply passage to adjust the internal environment of the culture space. The decontamination gas supply unit supplies decontamination gas into the culture space. The decontamination gas suction unit, which is provided upstream from the filter in the supply passage, sucks the decontamination gas out of the culture space and discharges the decontamination gas outside after it passes through the filter. The open air introduction unit, which is provided upstream from the filter in the supply passage, allows open air to enter the supply passage, pass through the filter, and enter the culture space. The decontamination gas, which is sucked by the decontamination gas suction unit and adsorbed onto the filter, is then backwashed by the open air introduced by the open air introduction unit and discharged into the culture space.

The decontamination gas suction unit and the open air introduction unit comprise a single gas supply/exhaust passage connected upstream from the filter in the supply passage, and a single pump provided in the gas supply/exhaust passage, for example. A catalyst may be provided in a supply/exhaust opening of the gas supply/exhaust passage to detoxify the decontamination gas.

Further, according to the present invention, there is provided a method for decontaminating an incubator including an environment-adjusting-medium supply unit and a decontamination gas supply unit. The environment-adjusting-medium supply unit has a supply passage, through which the environment-adjusting-medium stored in a reservoir is supplied to a culture space accommodating a cultured object. The environment-adjusting-medium is supplied from the reservoir to the culture space through a filter arranged in the supply passage to adjust the internal environment of the culture space. The decontamination gas supply unit supplies decontamination gas into the culture space. The method comprises sucking the decontamination gas supplied into the culture space through the supply passage, to discharge the decontamination gas outside after passing through the filter, and introducing open air into the supply passage upstream from the filter to allow the open air to pass through the filter, whereby the decontamination gas adsorbed on the filter is separated from the filter and is discharged into the culture space.

BRIEF DESCRIPTION OF THE DRAWINGS

The object and advantages of the present invention will be better understood from the following description, with reference to the accompanying drawings in which.

DESCRIPTION OF THE PREFERRED EMBODIMENTS

With reference to the drawings showing the embodiments, the present invention will be described below. An incubator 2 of a first embodiment is formed with a culture space 6 accommodating a cultured object such as cells to be cultivated, in a metal housing 4.

Figure 1:
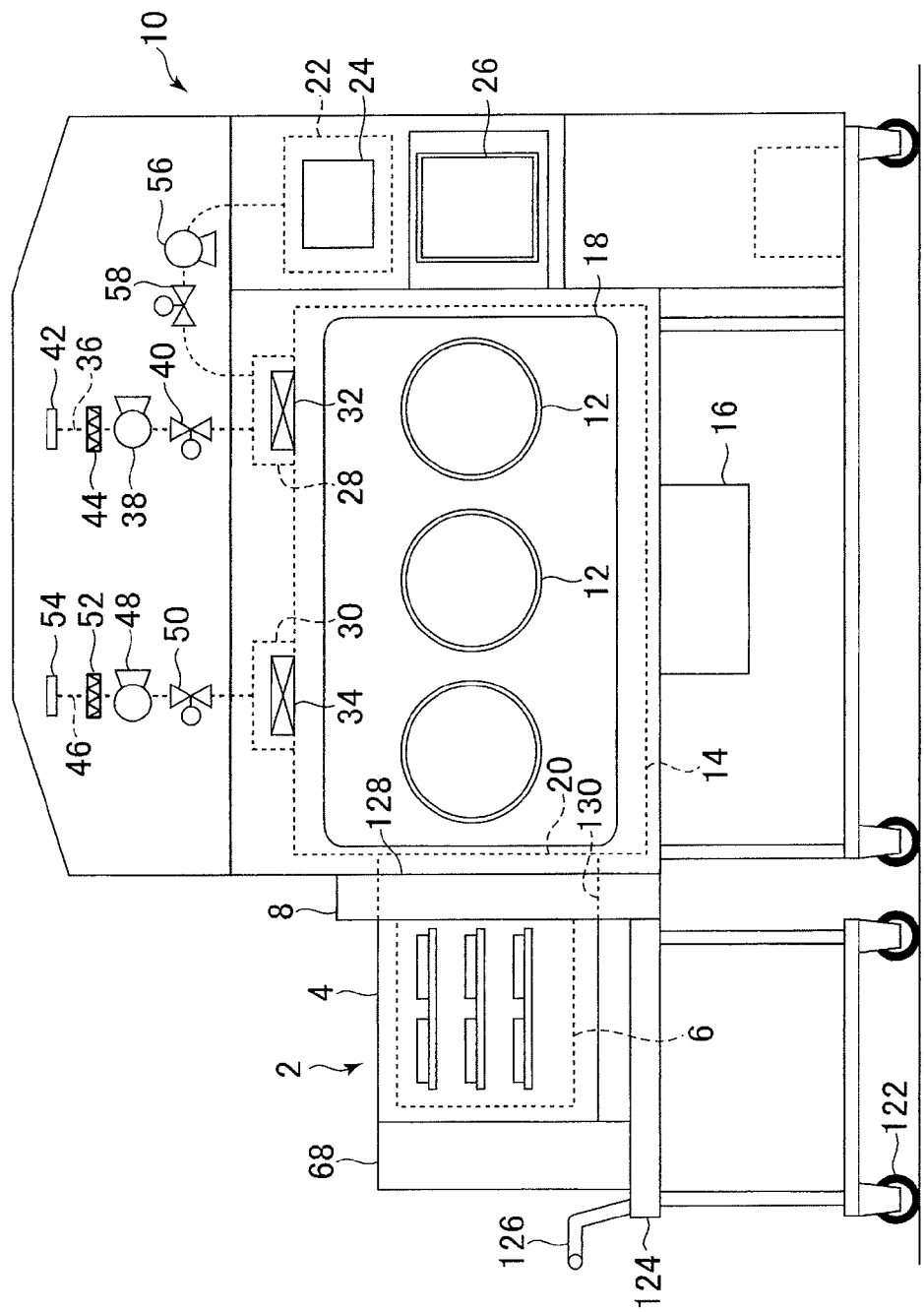
FIG. 1 is a front view showing a state in which an incubator of a first embodiment of the present invention, is connected to an isolator.

The incubator 2 is connected to an isolator 10 through an aseptic connection device 8. The isolator 10 has an operation room 14 inside of which the operator can access from the outside the operation room 14 through the use of gloves 12, which the operator can manipulate to separate and extract cells and so on, which are the cultured object, using equipment such as a centrifugal separator provided in the operation room 14. A transparent window 18 is provided in a front side of the isolator 10, so that the operator can see inside of the operation room 14 while carrying out operations. A door 20 (shown by a broken line) is provided on the left side of the isolator 10 in FIG. 1, and by opening the door 20, the operation room 14 can be accessed. The incubator 2 is connected to the door 20 through the aseptic connection device 8.

A decontamination gas generation device 22, which generates decontamination gas ($H_2O_2$ gas, for example) for decontaminating the inside of the operation room 14, is housed in the isolator 10. A container, in which an aqueous solution of decontamination gas is reserved, is inserted into the decontamination gas generation device 22 through a door 24 provided in the front side. The decontamination gas generation device 22 converts the aqueous solution of decontamination gas into decontamination gas, which is supplied into the operation room 14.

A pass-box 26 is connected to the operation room 14 through a door (not shown), which can open and close. While the door is closed, cultivating material hermetically enclosed in an aseptic container is housed in the pass-box, and decontamination gas is supplied from the decontamination gas generation device 22 into the pass-box 26 to sterilize the container. After that, the door is opened, and the container is transferred into the operation room 14. The cultivating material is then picked up from the container in the operation room 14.

An aeration filter box 28 and an exhaust filter box 30 are provided in an upper portion of the operation room 14, and HEPA filters 32 and 34 are housed in the aeration filter box 28 and the exhaust filter box 30. A gaseous body supplied to the filter boxes 28 and 30 is sterilized bypassing through the HEPA filters 32 and 34.

The aeration filter box 28 is connected to an aeration pipe 36, to which a pump 38 and a valve 40 are provided. By driving the pump 38, the air sucked through an aeration opening 42 is fed to the aeration filter box 28 through a catalyst 44, and supplied into the operation room 14 through the HEPA filter 32. The exhaust filter box 30 is connected to an exhaust pipe 46, to which a pump 48 and a valve 50 are provided. By driving the pump 48, the gaseous body sucked from the operation room 14 through the HEPA filter 34 is discharged from an exhaust opening 54 through a catalyst 52, in a detoxified state.

By controlling the aeration system and the exhaust system, the pressure in the operation room 14 can be adjusted. In this embodiment, the pressure in the operation room 14 is maintained at a the positive pressure, so that bacteria and so on is prevented from flowing into the operation room 14. Note that, in this embodiment, the decontamination gas generation device 22 is connected to the aeration filter box 28 through a pump 56 and a valve 58.

Figure 2:
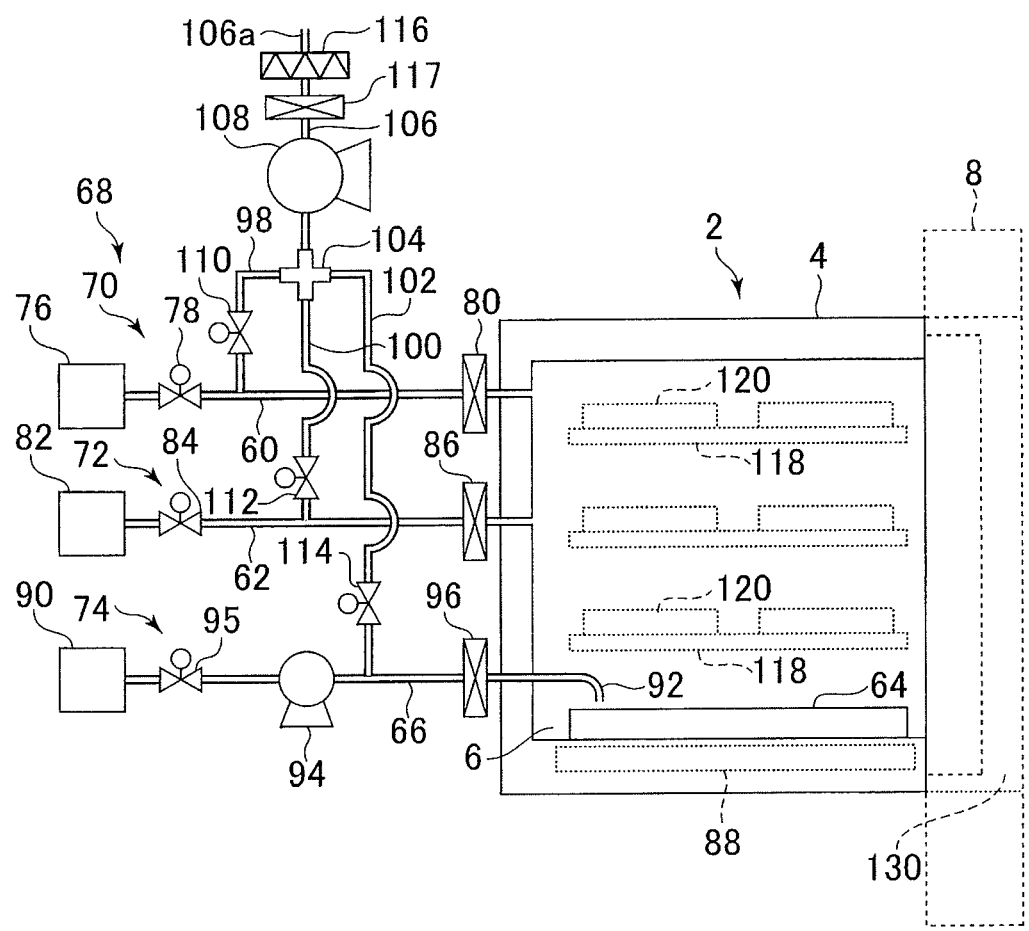
FIG. 2 is a circuit diagram showing a construction of an environment-adjusting-medium supply device of the incubator.

The incubator 2 is provided with gas supply passages 60 and 62 (see FIG. 2), through which carbon dioxide gas ($CO_2$ gas) and nitrogen gas ($N_2$ gas) of a predetermined concentration are supplied, and a humidification water supply passage 66, through which water for humidification is supplied to a water holding tray 64 disposed in the culture space 6, in order to adjust the inside of the culture space 6 formed in the incubator 2 to the environment suitable for the cell culture. An environment-adjusting-medium supply device 68, which supplies $CO_2$ gas, $N_2$ gas, and water for humidification (hereinafter, referred to as the environment-adjusting-media), is attached to the left side of the incubator 2 in FIG. 1. Supply devices 70, 72, and 74, included in the environment-adjusting-medium supply device 68, which supply the environment-adjusting-media to the culture space 6, are indicated in FIG. 2.

The $CO_2$ gas supply device 70 has a $CO_2$ gas supply passage 60 connecting a $CO_2$ gas tank 76 to the culture space 6 of the incubator 2. A flow regulating valve 78 and a HEPA filter 80 are provided in the supply passage 60, and $CO_2$ gas is supplied into the culture space 6 though the HEPA filter 80. The $N_2$ gas supply device 72 has a $N_2$ gas supply passage 62 connecting an $N_2$ gas tank 82 to the culture space 6. A flow regulating valve 84 and a HEPA filter 86 are provided in the $N_2$ gas supply passage 62, and $N_2$ gas is supplied into the culture space 6 though the HEPA filter 86.

A water reservoir (a water holding tray 64) storing water for humidification is arranged on a bottom portion of the culture space 6. Note that the water holding tray 64 is not shown in FIG. 1. A heater 88 is disposed under the water holding tray 64. Water supplied from a humidification water supply device 74 described below is heated and vaporized by the heater 88, so that the inside of the culture space 6 is maintained at a predetermined humidity.

The humidification water supply device 74 supplying water for humidification to the water holding tray 64 has a humidification water supply passage 66 connected to a water tank 90 disposed outside the incubator 2. The tip portion of the humidification water supply passage 66, which passes through a side wall of the housing 4 and is inserted in the culture space 6, is attached to a water supply nozzle 92 that faces the upper face of the water holding tray 64. The humidification water supply passage 66 is provided with a pump 94 and a solenoid valve 95, so that water for humidification can be supplied to the water holding tray 64 by opening the solenoid valve 95 and driving the pump 94. A HEPA filter 96 is provided to the furthest downstream portion of the humidification water supply passage 66 (close to the incubator 2). Note that, when water for humidification stored in the water tank 90 is sterilized water, the HEPA filter 96 can be replaced with a simple filter.

Divergent passages 98, 100, and 102 are provided upstream of the HEPA filters 80, 86, and 96 in the $CO_2$ gas supply passage 60, $N_2$ gas supply passage 62, and humidification water supply passage 66, respectively. These three divergent passages 98, 100, and 102 converge to a single gas supply/exhaust passage 106 through a pipe joint 104. A pump 108 is connected to the supply/exhaust passage 106, and by an operation of the pump 108, a gaseous body is supplied to or discharged from the gas supply passages 60 and 62 and the humidification water supply passage 66 through the divergent passages 98, 100, and 102, which are provided with flow regulating valves 110, 112, and 114. A catalyst 116 and a HEPA filter 117 are provided in a supply/exhaust opening 106a of the gas supply/exhaust passage 106, so that the gaseous body is supplied or exhausted through the catalyst 116 and the HEPA filter 117.

A plurality of racks 118 are provided in the culture space 6 of the incubator 2. Cultivation containers 120 such as a petri dish are placed on the racks 118, and the cultivation of cells is carried out.

The housing 4 of the incubator 2 having the culture space 6 therein and the environment-adjusting-medium supply device 68 are disposed on a hand truck 124 with casters 122, and can be moved manually using a handle 126 attached to the hand truck 124. The incubator 2, in which the door 128 is closed, and the isolator 10, in which the door 20 is closed, are connected to each other through the aseptic connection device 8. Under the connecting condition, the door 128 of the incubator 2 and the door 20 of the isolator 10 are open, thus enabling communication between the culture space 6 of the incubator 2 and the operation room 14 of the isolator 10.

Although the aseptic connection device 8 is not described in detail in this specification, as disclosed in Japanese Patent Publication No. 2011-50289, the aseptic connection device 8 has a hermetic mechanism, which encloses the door 128 of the incubator 2 and the door 20 of the isolator 10 to form a connection space 130 that is isolated from the ambient air.

An operation of the incubator 2 is described below. First, the incubator 2 is moved into position where the side of the door 128 is connected to the side of the door 20 of the isolator 10 through the aseptic connection device 8. Under this condition, the door 128 and the door 20 of the isolator 10 are opened, and thus decontamination gas ($H_2O_2$ gas) is supplied from the decontamination gas generation device 22 into the operation room 14. Further, the decontamination gas is introduced from the isolator 10 into the culture space 6 of the incubator 2 to decontaminate the inside of the culture space 6. Thus, when decontaminating the inside of the culture space 6, the pump 108 provided in the supply/exhaust passage 106 is driven in the forward direction to suck the decontamination gas into the culture space 6 to decontaminate the culture space 6.

When the pump 108 of the supply/exhaust passage 106 is driven to suck gaseous matter from the inside of the culture space 6, decontamination gas introduced from the operation room 14 of the isolator 10 into the culture space 6 passes through each of the supply passages for the environment-adjusting-media (i.e., the $CO_2$ gas supply passage 60, the $N_2$ gas supply passage 62, and the humidification water supply passage 66), through each of the divergent passages 98, 100, and 102, and then flows together at the supply/exhaust passage 106; thus the $H_2O_2$ gas is resolved, detoxified, and then discharged outside. At this time, since the decontamination gas passes through the HEPA filters 80, 86, and 96 provided on the side of the incubator 2 in each of the supply passages 60, 62, and 66, each of the HEPA filters 80, 86, and 96 is decontaminated by adsorbing the decontamination gas.

After that, the supply of the decontamination gas from the decontamination gas generation device 22 is stopped, and the pump 38 of the isolator 10 is driven to introduce open air into the operation room 14 through the HEPA filter 32, by which the open air is sterilized, so that the decontamination gas is discharged from the operation room 14 (i.e., aeration). The sterilized air is also introduced into the culture space 6 of the incubator 2, and thus the aeration is performed so that the decontamination gas is discharged from the culture space 6. At this time, the pump 108 of the supply/exhaust passage 106, which is connected to each of the supply passages 60, 62, and 66 of the environment-adjusting-medium supply device 68, is rotated in the reverse direction and open air is introduced into the culture space 6. The open air fed by the pump 108 flows from each of the divergent passages 98, 100, and 102 to each of the supply passages 60, 62, and 66, passes through the HEPA filters 80, 86, and 96 provided downstream of each of the supply passages 60, 62, and 66, and then enters the culture space 6. Due to this, the decontamination gas adsorbed on the HEPA filters 80, 86, and 96 when decontaminating the culture space 6 is backwashed by the open air, separated from the HEPA filters, and discharged into the culture space 6.

After carrying out the decontamination and the aeration of the operation room 14 of the isolator 10 and the culture space 6 of the incubator 2, which are connected to each other, a cultured object such as cells subjected to predetermined operations in the operation room 14 can be placed in a container and then accommodated in the culture space 6 of the incubator 2.

After the container, in which the cells and so on have been placed, is transferred from the operation room 14 of the isolator 10 to the culture space 6 of the incubator 2, the door 128 of the incubator 2 is closed from the operation room 14. Under the condition in which the culture space 6 is hermetically sealed, water is supplied from the humidification water supply device 74 to the water holding tray 64, and the heater 88 is actuated so that the humidity in the culture space 6 is raised at a predetermined temperature. Further, $CO_2$ gas and $N_2$ gas, which compose the environment-adjusting media, are supplied to the culture space 6 from the $CO_2$ gas supply device 70 and the $N_2$ gas supply device 72 of the environment-adjusting-medium supply device 68, so that $CO_2$ gas and $N_2$ gas can be maintained in the culture space 6 at predetermined levels for a predetermined period of time to enable the cultivation of the cells.

After closing the door 128, the incubator 2 is separated from the isolator 10 and moved to a predetermined position. Once the cultivation has been carried out while maintaining the environment in the culture space 6 for a predetermined time period, the incubator 2 is moved and connected to the isolator 10 again, and the cells and so on, which have been cultured, are transferred from the culture space 6 of the incubator 2 into the operation room 14 of the isolator 10, where the cells and so on can be enclosed in a sterilized container in the operation room 14.

Figure 3:
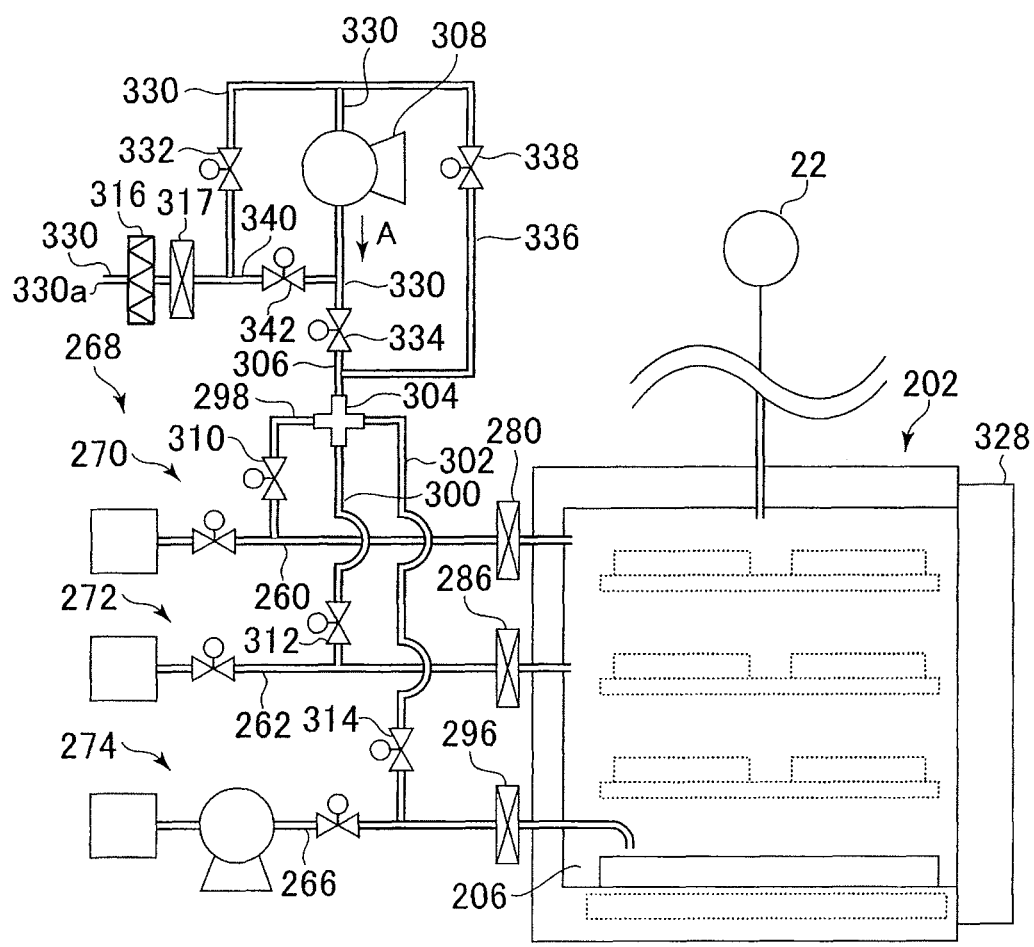
FIG. 3 is a circuit diagram showing a construction of the environment-adjusting-medium supply device of the incubator of a second embodiment.

FIG. 3 shows an incubator 202 of a second embodiment. Similarly to the first embodiment, when decontaminating the inside of a culture space 206 of an incubator 202, HEPA filters 280, 286, 296 provided at the downstream ends of each of the supply passages 260, 262, and 266 of an environment-adjusting-medium supply device 268 are decontaminated, and the decontamination gas is then removed from the HEPA filters 280, 286, and 296. In the second embodiment, however, the structure of the plumbing used in the suction of the decontamination gas from the culture space 206 and the introduction of open air into the culture space 206 is different.

Also in the second embodiment, a $CO_2$ gas supply device 270, an $N_2$ gas supply device 272, and a humidification water supply device 274 forming an environment-adjusting-medium supply device 268 are provided with HEPA filters 280, 286, and 296 at downstream ends (close to the incubator 202)

of the supply passages 260, 262, and 266. Further, divergent passages 298, 300, and 302 are connected to the supply passages 260, 262, and 266, and converge into a single gas supply/exhaust passage 306 through an intersection joint 304. The divergent passages 298, 300, and 302 are provided with the flow regulating valves 310, 312, and 314, similarly to the first embodiment.

Although the single supply/exhaust passage 106 extends directly to the supply/exhaust opening 106*a* in the first embodiment, a pump 308 is provided, and bypass passages 336, 340 are connected to a main passage 330, which is connected to a supply/exhaust opening 330*a* through a catalyst 316 and a HEPA filter 317, in the second embodiment. The main passage 330 is provided with a first valve 332 upstream of the pump 308 (between the pump 308 and a catalyst 316) and a second valve 334 downstream of the pump 308 (between the pump 308 and the intersection joint 304). The first bypass passage 336, which communicates a portion between the second valve 334 and the pipe joint 304 with a portion between the pump 308 and the first valve 332, is provided with a third valve 338. Further, the second bypass passage 340 communicating a portion between the pump 308 and the second valve 334 with a portion between the first valve 332 and the catalyst 316 is provided, and a fourth valve 342 is provided on the second bypass passage 340.

The rotational direction of the pump 308 is constant and always feeds the gaseous body in a downstream direction indicated by arrow A, and the suction of the decontamination gas from the culture space 206 and the supply of open air into the culture space 206 are changed by opening and closing each of the valves 332, 334, 338, and 342.

When decontaminating the inside of the culture space 206 of the incubator 202, the first valve 332 and the second valve 334 provided on the main passage 330 are closed, and the third valve 338 of the first bypass passage 336 and the fourth valve 342 of the second bypass passage 340 are open. If the pump 308 is driven in this state, the decontamination gas sucked from the culture space 206 flows into the gas supply/exhaust passage 306 from the supply passages 260, 262, and 266, and the divergent passages 298, 300, and 302. However, since the second valve 334 and the first valve 332 of the main passage 330 are closed, the decontamination gas passes through the bypass passage 336, a portion of the main passage 330 provided with the pump 308, and the second bypass passage 340 before being discharged to the outside through the catalyst 316 and the HEPA filter 317. At this time, the decontamination gas passes through the HEPA filters 280, 286, and 296 of the supply passages 260, 262, and 266, and thus the HEPA filters 280, 286, and 296 are decontaminated.

After the decontamination of the culture space 206 is completed, the system can be aerated by opening the first valve 332 and the second valve 334 of the main passage 330, closing the third valve 338 of the first bypass passage 336 and the fourth valve 342 of the second bypass passage 340, and driving the pump 308. Although the discharging direction A of a gaseous body from the pump 308 is constant, open air introduced from the supply/exhaust opening 330*a*, which is sterilized by passing through the catalyst 316 and the HEPA filter 317, passes through the main passage 330 into the divergent passages 298, 300, and 302 from the gas supply/exhaust passage 306, and further flows into the supply passages 260, 262, and 266 through the HEPA filters 280, 286, and 296 to enter the culture space 206. Thus, open air is supplied into the culture space 206 through the HEPA filters 280, 286, and 296, and thus the decontamination gas, which has been adsorbed on the HEPA filters 280, 286, and 296, is separated therefrom, and is discharged into the culture space 206.

Note that, in the first embodiment, the decontamination gas supplied into the operation room 14 from the decontamination gas generation device 22 provided in the isolator 10 is introduced into the culture space 6 connected to the operation room 14 to decontaminate the culture space 6. Conversely, in the second embodiment, as indicated on an upper portion of FIG. 3, the decontamination gas generation device 22 of the isolator 10 may be connected to the incubator 202, so that the decontamination can be performed separately in the operation room 14 of the isolator 10 and the culture space 206 of the incubator 202 while the door 328 of the isolator 10 is closed. Further, a decontamination gas generation device may be connected to the incubator 202 independently from the isolator 10. The same effects can be obtained by the second embodiment as the first embodiment. Note that, in the second embodiment, the isolator and the decontamination gas supply device are described using the same references as the first embodiment.

Figure 4:
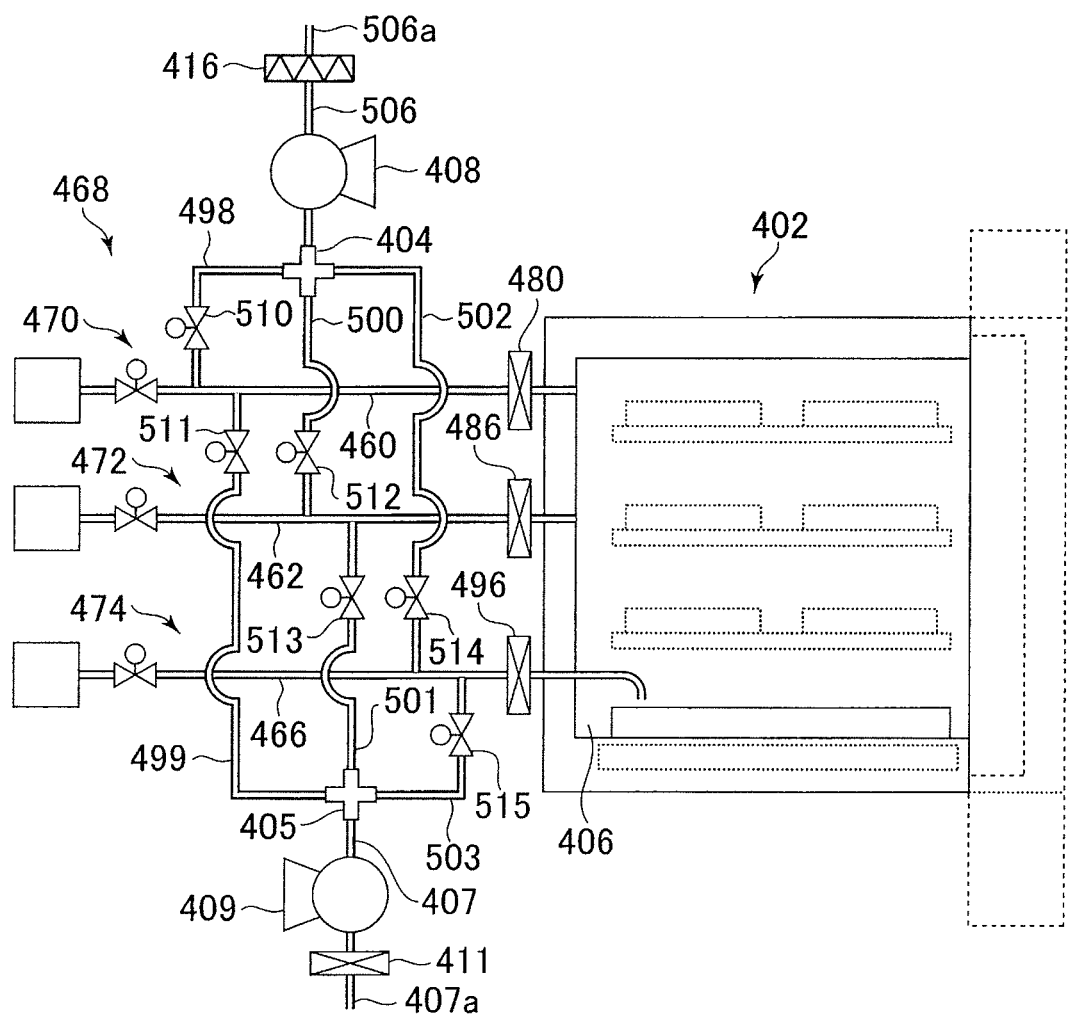
FIG. 4 is a circuit diagram showing a construction of the environment-adjusting-medium supply device of the incubator of a third embodiment.

FIG. 4 is a view showing a circuit for the decontamination and aeration of an incubator 402 of a third embodiment, in which plumbing for decontamination and aeration are separately provided. In this embodiment, two divergent pipes are provided to portions upstream from HEPA filters 480, 486, and 496 of supply passages 460, 462, and 466 connected to a $CO_2$ gas supply device 470, an $N_2$ gas supply passage 472, and a humidification water supply device 474 of an environment-adjusting-medium supply device 468.

One group of three divergent passages 498, 500, and 502 (extending upward in FIG. 4), which are provided for decontamination, are connected to the supply passages 460, 462, and 466 and converge into a single exhaust passage 506 through an intersection joint 404. A decontamination pump 408 is connected to the exhaust passage 506, in which a catalyst 416 is provided on the side of an exhaust opening 506*a*. Another group of three divergent passages 499, 501, and 503 (extending downward in FIG. 4), which are provided for aeration, are connected to the supply passages 460, 462, and 466 and converge into a single aeration passage 407 through an intersection joint 405. The aeration passage 407 is provided with an aeration pump 409 and HEPA filter 411, and open air is sucked in through an intake opening 407*a* by driving the pump 409. The divergent passages 498, 500, 502, 499, 501, and 503 are provided with flow regulation valves 510, 512, 514, 511, 513, and 515.

When decontaminating the inside of the culture space 406 of the incubator 402, the decontamination gas is supplied from the decontamination supply device (not shown) to the culture space 406, and the decontamination pump 408 sucks the decontamination gas out of the culture space 406. The decontamination gas pumped out of the culture space 6 passes through the HEPA filters 480, 486, and 496 connected to the supply passages 460, 462, and 466, and enters the divergent passages 498, 500, and 502. The decontamination gas then converges into the exhaust passage 506 through the pipe joint 404, and is detoxified by passing through the catalyst 416 before being discharged through the exhaust opening 506*a*.

When aeration of the culture space 406 is carried out, the aeration pump 409 is driven, and thus open air sterilized by the HEPA filter 411 is fed to the divergent passages 499, 501, and 503. The open air then passes through the supply passages 460, 462, and 466, and is supplied to the culture space 406, where aeration is performed. At this time, open air passes through the HEPA filters 480, 486, and 496 connected to the supply passages 460, 462, and 466, so that the contamination gas, which has been adsorbed on these HEPA filters 480, 486, and 496, is separated therefrom, and is discharged into the culture space 406. In the third embodiment, the same effects are obtained as those of the first and second embodiments.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2013-237995 (filed on Nov. 18, 2013) which is expressly incorporated herein, by reference, in its entirety.

The invention claimed is:

1. An incubator comprising:
 an environment-adjusting-medium supply unit having a supply passage through which the environment-adjusting-medium stored in a reservoir is supplied to a culture space accommodating a cultured object, the environment-adjusting-medium supply unit supplying the environment-adjusting-medium from the reservoir to the culture space through a filter arranged in the supply passage to adjust the internal environment of the culture space;
 a decontamination gas supply unit that supplies decontamination gas into the culture space;
 a decontamination gas suction unit that is provided upstream from the filter in the supply passage to suck the decontamination gas out of the culture space and discharge the decontamination gas outside after passing through the filter; and
 an open air introduction unit that is provided upstream from the filter in the supply passage to allow open air to enter the supply passage, pass through the filter, and enter the culture space;
 the decontamination gas, which is sucked by the decontamination gas suction unit and adsorbed onto the filter, being backwashed by the open air introduced by the open air introduction unit and discharged into the culture space.

2. The incubator according to claim 1, wherein the decontamination gas suction unit and the open air introduction unit comprise a single gas supply/exhaust passage connected to a portion upstream from the filter in the supply passage, and a single pump provided in the gas supply/exhaust passage.

3. The incubator according to claim 2, further comprising a catalyst in a supply/exhaust opening of the gas supply/exhaust passage to detoxify the decontamination gas.

* * * * *